US008747814B2

(12) United States Patent
Rajaiah et al.

(10) Patent No.: US 8,747,814 B2
(45) Date of Patent: *Jun. 10, 2014

(54) ORAL CARE COMPOSITIONS AND METHODS

(75) Inventors: Jayanth Rajaiah, Loveland, OH (US); Arif Ali Baig, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 242 days.

This patent is subject to a terminal disclaimer.

(21) Appl. No.: 12/857,620

(22) Filed: Aug. 17, 2010

(65) Prior Publication Data

US 2011/0038810 A1 Feb. 17, 2011

Related U.S. Application Data

(60) Provisional application No. 61/234,512, filed on Aug. 17, 2009, provisional application No. 61/255,926, filed on Oct. 29, 2009, provisional application No. 61/241,564, filed on Sep. 11, 2009.

(51) Int. Cl.
*A61K 8/31* (2006.01)
*A61Q 11/00* (2006.01)

(52) U.S. Cl.
USPC .............................. 424/49; 424/57; 424/401

(58) Field of Classification Search
None
See application file for complete search history.

(56) References Cited

U.S. PATENT DOCUMENTS

| | | | |
|---|---|---|---|
| 2,574,476 A | | 8/1950 | Heath et al. |
| 4,152,421 A | * | 5/1979 | Tsutsumi et al. ............... 424/57 |
| 4,292,028 A | | 9/1981 | Barr |
| 4,918,103 A | * | 4/1990 | Park et al. ..................... 514/520 |
| 5,130,122 A | | 7/1992 | Tabibi et al. |
| 5,260,051 A | * | 11/1993 | Cho ................................. 424/57 |
| 5,310,563 A | | 5/1994 | Curtis et al. |
| 5,370,865 A | * | 12/1994 | Yamagishi et al. .............. 424/54 |
| 5,605,676 A | * | 2/1997 | Gaffar et al. ..................... 424/49 |
| 5,639,445 A | | 6/1997 | Curtis et al. |
| 5,700,478 A | | 12/1997 | Biegajski et al. |
| 5,980,868 A | | 11/1999 | Homola et al. |
| 5,989,522 A | | 11/1999 | Friedman |
| 6,383,475 B1 | | 5/2002 | Meyers et al. |
| 6,500,406 B1 | | 12/2002 | Rajaiah et al. |
| 6,517,350 B2 | | 2/2003 | Diasti et al. |
| 6,617,374 B1 | | 9/2003 | Rajaiah et al. |
| 6,660,776 B1 | | 12/2003 | McDaniels, III |
| 6,673,358 B1 | * | 1/2004 | Cole et al. ..................... 424/404 |
| 6,706,256 B2 | | 3/2004 | Lawlor |
| 6,905,694 B1 | | 6/2005 | Modi |
| 6,916,463 B2 | | 7/2005 | Lee et al. |
| 7,832,956 B2 | | 11/2010 | Ross |
| 2003/0003060 A1 | * | 1/2003 | McDaniels, III ............... 424/49 |
| 2003/0072841 A1 | * | 4/2003 | Rajaiah et al. ..................... 426/3 |
| 2003/0091540 A1 | | 5/2003 | Ahmad et al. |
| 2003/0161851 A1 | | 8/2003 | Breha, III et al. |
| 2004/0137021 A1 | | 7/2004 | De La Poterie et al. |
| 2005/0196355 A1 | | 9/2005 | Georgiades et al. |
| 2005/0281757 A1 | * | 12/2005 | Ibrahim et al. .................. 424/49 |
| 2006/0177384 A1 | * | 8/2006 | Brown ............................. 424/49 |
| 2006/0198799 A1 | | 9/2006 | Giniger |
| 2006/0239938 A1 | | 10/2006 | Perechocky |
| 2007/0037717 A1 | | 2/2007 | Clark et al. |
| 2007/0048339 A1 | | 3/2007 | Popplewell et al. |
| 2007/0183986 A1 | | 8/2007 | Alfred et al. |
| 2007/0190090 A1 | | 8/2007 | Brown |
| 2007/0286904 A1 | | 12/2007 | Popplewell et al. |
| 2007/0298061 A1 | | 12/2007 | Boghani et al. |
| 2008/0112902 A1 | | 5/2008 | Perechocky |
| 2011/0008400 A1 | | 1/2011 | Wagner |
| 2011/0058891 A1 | | 3/2011 | Ross |

FOREIGN PATENT DOCUMENTS

| | | | |
|---|---|---|---|
| JP | 08301743 A | * | 11/1996 |
| WO | WO 2004/073668 A1 | | 9/2004 |
| WO | WO 2004/073669 A1 | | 9/2004 |
| WO | WO 2004/073670 A1 | | 9/2004 |
| WO | WO 2004/073671 A1 | | 9/2004 |
| WO | WO 2004/073672 A1 | | 9/2004 |
| WO | WO 06/002957 A1 | | 1/2006 |
| WO | WO 07/079069 A1 | | 7/2007 |
| WO | WO 07/079170 A1 | | 7/2007 |
| WO | WO 08/016837 A2 | | 2/2008 |
| WO | WO 2011/000524 | | 1/2011 |

OTHER PUBLICATIONS

Japanese patent JP 08301743 A translation.*

* cited by examiner

*Primary Examiner* — Frederick Krass
*Assistant Examiner* — Isaac Shomer
(74) *Attorney, Agent, or Firm* — Armina E. Stricklin; Carrie A. Morgan

(57) ABSTRACT

Advantageous oral care composition can include a water insoluble carrier, sweetener, and an additional component selected from the group consisting of flavors, sensates, and combinations thereof, where the composition is configured for use in the oral cavity.

12 Claims, No Drawings

US 8,747,814 B2

ORAL CARE COMPOSITIONS AND METHODS

CROSS REFERENCE TO RELATED APPLICATION

The present application claims priority to U.S. provisional application Nos. 61/234,512 filed on Aug. 17, 2009; 61/255,926 filed on Oct. 29, 2009; and 61/241,564 filed Sep. 11, 2009; the disclosures of which are incorporated herein by reference.

FIELD OF THE INVENTION

This application relates to oral care compositions with a water insoluble component and varying combinations of sweetener, flavor, and/or sensate, and methods relating thereto.

BACKGROUND OF THE INVENTION

Historically, oral care products like dentifrices and rinses have been used for cleansing the oral cavity. Because these products often get their cleaning effect from surfactants and surfactants generally give a better result in a water based environment, these products generally utilize water soluble components as their base. For deposition, however, these water soluble chassis have several disadvantages. For one, the water soluble chassis are quickly washed away in the mouth due to interaction with saliva meaning the residence time for anything deposited in these chassis is often very short. As such, there is a need for oral care compositions and methods which give a better deposition profile in the oral cavity.

Additionally, in order to promote consumer use and acceptance, taste is an import aspect of an oral care product. Thus, consumer product companies work to not only provide a product with a benefit, but to make that product acceptable to the consumer. Thus, there is a need for improved flavor combinations for oral care products.

SUMMARY OF THE INVENTION

One embodiment of the present invention is directed to an oral care composition, consisting essentially of a water insoluble carrier, a sweetener, and an additional component selected from the group consisting of a sensate, a flavor, and combinations thereof. The oral care composition is configured for application within the oral cavity.

According to another embodiment, the present invention is directed to an oral care composition which includes from about 50% to about 99% of a water insoluble carrier, from about 0.5% to about 10% a sweetener, and an additional component selected from the group consisting of a sensate, a flavor, and combinations thereof. The oral care composition is configured for application to the teeth.

In yet another embodiment, the present invention is directed to an oral care composition, consisting essentially of: petrolatum; saccharin; mint oil; and menthol. The oral care composition is configured for application to the teeth.

These and other embodiments will be better understood in light of the disclosure below.

DETAILED DESCRIPTION

Definitions

The term "sensate" as used herein refers to a material in which its predominant effect in the oral cavity is to impart a sensation, for example, a warming, cooling, and/or tingling sensation.

The term "flavor" as used here refers to a material in which its predominant effect in the oral cavity is to impart a taste, excluding sweeteners.

The term "sweetener" as used herein refers to a material in which its predominant effect in the oral cavity is to impart a sweet taste.

The term "water-insoluble" as used herein refers to a material that is less than about 10% soluble in water, unless specifically stated otherwise.

All percentages and ratios herein are by weight of total composition, unless otherwise indicated.

DESCRIPTION OF THE INVENTION

Oral care products have variable functions within the oral cavity. For instance, when looking to clean the oral cavity, a consumer will generally look to toothpaste or a mouth rinse. To provide this cleaning benefit, both pastes and rinses generally use a foaming water soluble chassis. The foam provided in these chassis provides a cleaning action which can be used in combination with a brush or actives to provide a further cleaning benefit. Other oral care products provide more of an aesthetic function, like breath freshening. These products come in many forms from dissolvable strips to mints. The one thing most all of these products have in common is that they are generally water soluble. The water soluble nature of these products limits the length of time for which they can provide their benefit as the benefit providing components are solubilized and/or washed away by the saliva in the oral cavity.

It has now been surprisingly discovered that water insoluble carriers can be used in oral care compositions to give improved delivery of oral care components to the oral cavity. Some of these oral care components include, for example, sensates, flavors, and sweeteners. The use of the water insoluble carrier allows for a longer residence time in the oral cavity for the oral care components and thus provides a longer lasting benefit. For example, in some instances, the water-insoluble carrier can be detected in the mouth even an hour or more after application.

Water Insoluble Carrier

Water insoluble components can be used as a carrier in the present invention. In varying embodiments, the water insoluble carrier is less than about 10, %, 8%, 5%, 4%, 3%, 2% or 1% soluble in water. In one embodiment the water-insoluble carrier is at a level from about 25, 30, 35, 40, 45, 50, 55, 60, 65% to about 45, 50, 55, 60, 65, 70, 75, 80, 85, 90, 95, 99%, and/or any combination thereof, by weight of the composition. In varying embodiments the water-insoluble carrier level is from about 80% to about 99%, from about 80% to about 95%, or from about 85% to about 95% by weight of the composition. In another embodiment, the water insoluble carrier is at least about 75% by weight of the oral care composition. In yet another embodiment the water-insoluble carrier is both water-insoluble and substantially non-swellable in water. In other embodiments, the water insoluble carrier comprises a gel, liquid, or mixtures thereof. The water-insoluble carrier may be a combination of two or more water-insoluble components.

In one embodiment, the water insoluble carrier is selected from the group consisting of: natural wax, synthetic wax, petrolatum, rubber, elastomer, plastomer, polyvinyl chloride, nylon, polyvinyl acetate, natural oils, synthetic oils, fats, silicone, hydrocarbons, essential oils, caprilic/capric triglycerides, polybutene, oleic acid, stearic acid, fluorocarbon, polyurethane prepolymer, polyethylene, polystyrene, polypropylene, and mixtures thereof. In another embodiment the water-insoluble carrier is a PDMS gum, or a mixture of PDMS gum with an MQ resin cast from a solvent such as volatile isoparrafin (see U.S. Pat. No. 6,074,654).

In one embodiment the water-insoluble carrier comprises a natural wax, synthetic wax, or a combination thereof. Natural waxes include, for example, animal, vegetable, and mineral wax. Animal waxes include, for example, beeswax, lanolin, shellac wax, Chinese wax, etc. Vegetable waxes include carnauba, candelilla, bayberry, sugar cane, etc., and mineral waxes include fossil and earth waxes (ozocerite, ceresin, montan), and petroleum waxes such as paraffin, microcrystalline, etc. In one embodiment the waxes herein are natural waxes selected from the group consisting of beeswax, candelilla, candela, carnauba, paraffin, microcrystalline wax, Fischer-Tropsch waxes, and mixtures thereof.

Examples of natural oils include, but are not limited to, vegetable oils (ex. corn oil), soy bean oils, cottonseed oils, palm oils, coconut oils, mineral oils, animal oils (ex. fish oils), etc. Examples of synthetic oils include, but are not limited to, silicone oils, etc. In one embodiment, the water insoluble component comprises a natural oil. In a further embodiment, the natural oil comprises mineral oil. In one embodiment, mineral oil is present in the composition at an amount from about 30% to about 50% and in another embodiment, from about 35% to about 45%.

Examples of elastomers include, but are not limited to, Ethylene-Ethylene-Propylene rubber, Ethylene-Propylene rubber, Styrene-Ethylene—Propylene-Styrene rubber, and combinations thereof, and these may optionally be further combined with waxes.

In one embodiment, the water insoluble carrier comprises microcrystalline wax, paraffin wax, bees wax, petrolatum, mineral oil, polybutene, silicone, natural oil, synthetic oil, polyethylene, or combinations thereof. In a further embodiment, the water insoluble carrier is selected from the group consisting of polybutene, silicones, petrolatum, and combinations thereof. In another embodiment, the carrier comprises petrolatum. In yet another embodiment, the carrier consists essentially of petrolatum.

While several specific embodiments of water insoluble carriers are listed herein, it is envisioned other suitable combinations are also possible and within the scope of invention.

Sensates

The present invention may include one or more components that provide a sensory benefit, often called a sensate. Sensates can have sensory attributes such as a warming, tingling, or cooling sensation. Suitable sensates include, for example, menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal known as CGA, and mixtures thereof.

In one embodiment, the sensate comprises a coolant. The coolant can be any of a wide variety of materials. Included among such materials are carboxamides, menthol, ketals, diols, and mixtures thereof. Some examples of carboxamide coolants include, for example, paramenthan carboxyamide agents such as N-ethyl-p-menthan-3-carboxamide, known commercially as "WS-3", N,2,3-trimethyl-2-isopropylbutanamide, known as "WS-23," and N-(4-cyanomethylphenyl)-ρ-menthanecarboxamide, known as G-180 and supplied by Givaudan. G-180 generally comes as a 7.5% solution in a flavor oil, such as spearmint oil or peppermint oil. Examples of menthol coolants include, for example, menthol; 3-1-menthoxypropane-1,2-diol known as TK-10, manufactured by Takasago; menthone glycerol acetal known as MGA manufactured by Haarmann and Reimer; and menthyl lactate known as Frescolat® manufactured by Haarmann and Reimer. The terms menthol and menthyl as used herein include dextro- and levorotatory isomers of these compounds and racemic mixtures thereof.

In one embodiment, the sensate comprises a coolant selected from the group consisting of menthol; 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-ρ-menthanecarboxamide, and combinations thereof. In a further embodiment, the sensate comprises menthol; N,2,3-trimethyl-2-isopropylbutanamide; N-(4-cyanomethylphenyl)-ρ-menthanecarboxamide; or a combination thereof. In one embodiment, the sensate comprises menthol. In another embodiment, the sensate consists essentially of menthol.

The amount of sensate employed is normally a matter of preference subject to such factors as type and strength of effect desired. Sensates can be present in amounts up to about 40% by weight of the oral care composition. In varying embodiments, the sensates can be present from about 0.1, 0.5, 1, 2, 3, 4, 5, 6, 7, 8, 9, or 10%, to about 2, 5, 6, 7, 8, 9, 10, 12, 15, 20, 30, or 40%, or any combination thereof. In varying embodiments, the sensate is present in an amount from about 0.1% to about 20.0%, from about 1% to about 10%, or from about 3% to about 6% by weight of the total composition.

Flavors

The present invention may include one or more components that provide a flavor benefit. The flavoring component can be chosen from natural and synthetic flavorings. Natural flavors can include, for example, oils derived from plant leaves, flowers, fruits and so forth. Some representative flavorings include, for example, vanilla, sage, marjoram, parsley oil, spearmint oil, cinnamon oil, wintergreen oil (methylsalicylate), and peppermint oils. Also useful herein are artificial, natural or synthetic fruit flavors. These include, for example, citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. These can be in any form including liquid, powder, etc. Additionally, flavor adsorbed onto a hydrophilic matrix may be included, e.g. "spray-dried" flavors. Furthermore, encapsulated flavors may be included.

In one embodiment, the flavor is selected from mint, wintergreen, spice, vanilla, fruit, citrus, cocoa, tea, or a combination thereof. In one embodiment, the flavor component is selected from the group consisting of peppermint, spearmint, vanilla, cinnamon, wintergreen, mint, strawberry, grape, apple, and combinations thereof. In a further embodiment, the flavor component comprises mixed mint, peppermint, spearmint, wintergreen, or a combination thereof. In an additional embodiment, the flavor component comprises peppermint.

The amount of flavor employed is normally a matter of preference subject to such factors as type and strength of effect desired. Flavors can be present in amounts up to about 40%. In varying embodiments, the flavor can be present from about 0.1, 0.5, 1, 2, 3, 4, 5, 6, 7, 8, 9, or 10%, to about 2, 5, 6, 7, 8, 9, 10, 12, 15, 20, 30, or 40%, or any combination thereof. In varying embodiments, the flavor is present in an amount from about 0.1% to about 20.0%, from about 1% to about 10%, or from about 3% to about 6% by weight of the total composition.

Sweeteners

The present invention may include one or more components that provide a sweetening benefit. Suitable sweeteners include both natural and artificial sweeteners. The sweeteners can be water-soluble or water-insoluble. The sweetener may also be an intense sweetener.

Some examples of sweeteners include dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols such as sorbitol, xylitol, maltitol, isomalt, and hydrogenated starch.

Intense sweeteners are often dipeptide based. Some examples of intense sweeteners include monellin, haumatoccous danielli, and L-aspartyl L-phenylalanine methyl ester and soluble saccharin salts.

In one embodiment, the sweetener is selected from the group consisting of dextrose, sucrose, maltose, dextrin, dried invert sugar, mannose, xylose, ribose, glucose, fructose, levulose, galactose, corn syrup, high fructose corn syrup, corn syrup solids, partially hydrolyzed starch, aspartame, saccharin, sugar alcohols, hydrogenated starch, monellin, haumatoccous danielli, L-aspartyl L-phenylalanine methyl ester, soluble saccharin salts, and combinations thereof. In a another embodiment, the sweetener is selected from the group consisting of saccharin, sucralose, Rebiana, xylitol, aspartame, Acesulfame K, mono ammoniated glycyrrhizinate, and mixtures thereof. In another embodiment, the sweetener comprises saccharin, sucralose, Rebiana, or a combination thereof. In one embodiment, the sweetener comprises saccharin. In another embodiment, the sweetener consists essentially of saccharin.

The amount of the sweetener will vary with the type of sweetener selected and the desired level of sweetness. Sweeteners can be present in amounts up to about 20%. In other embodiments the sweeteners can be present from about 0.1, 0.15, 0.25, 0.5, 0.75, 1, 1.25, 1.5, 1.75, 2, 2.25, 2.5, 2.75, 3, 4, 5, or 10%, to about 1, 2, 3, 4, 5, 10, or 20%, or any combination thereof by weight of the oral care composition. In varying embodiments, the sweetener is present in an amount from about 0.1% to about 10.0%, from about 1% to about 5%, or from about 1.5% to about 3%, by weight of the total composition.

Other Components

In addition to those components listed above, the oral care composition may additionally include other components. One example of these additional components includes substantivity agents. One group of substantivity agents is organophosphates. Suitable organophosphate compounds have a strong affinity for the tooth surface and have sufficient surface binding propensity to desorb pellicle proteins and remain affixed thereon. The phosphate groups of the organophosphate attach themselves to cations, in particular calcium ions in teeth or some other positively charged sites such as protein residues on the mucosal surface and thus serve to anchor the hydrophobic portion of the molecule onto the surface thereby modifying it to be hydrophobic. The phosphate groups provide ready bonding/binding to cationic and charged surfaces via electrostatic interaction, hydrogen bonding, or complexation, which leads to ready deposition of the organophosphate upon application to form a coating on the treated surface. The strong bond results in longer retention or durability and substantivity of the coating.

Examples of suitable organophosphate compounds are mono-, di- or triesters represented by the following general structure wherein $Z^1$, $Z^2$, or $Z^3$ may be identical or different, at least one being an organic moiety, preferably selected from linear or branched, alkyl or alkenyl group of from 6 to 22 carbon atoms, optionally substituted by one or more phosphate groups; alkoxylated alkyl group or alkoxylated alkenyl group.

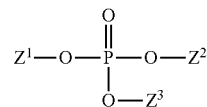

Some preferred agents include alkoxylated alkyl or alkenyl phosphate esters represented by the following structure:

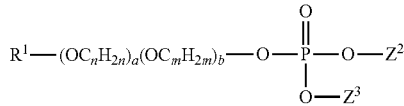

wherein $R^1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$—group. Preferably, $R^1$ is an alkyl group of at least 10 carbon atoms and a and b are each no more than 10 in order to maintain overall hydrophobic character of the organophosphate and the degree of hydrophobicity imparted to the surface.

In one embodiment, the substantivity agent includes mono- di- and tri-alkyl and alkyl (poly)alkoxy phosphates such as dodecyl phosphate, lauryl phosphate; laureth-1 phosphate; laureth-3 phosphate; laureth-9 phosphate; dilaureth-10 phosphate; trilaureth-4 phosphate; $C_{12-18}$ PEG-9 phosphate and salts thereof. Many are commercially available from suppliers including Croda; Rhodia; Nikkol Chemical; Sunjin; Alzo; Huntsman Chemical; Clariant and Cognis. In one embodiment, the substantivity agent comprises monoalkyl phosphate.

Another example of an additional component includes actives. Some examples of actives include various fluoride salts for caries prevention and remineralization; gingivitis prevention by the use of antimicrobial agents such as triclosan, cetylpyridinium chloride, stannous fluoride, zinc citrate or essential oils; and hypersensitivity control through the use of ingredients such as strontium chloride, stannous fluoride, or potassium nitrate; pyrophosphate salts can be used as antitartar agents; peroxides can be used for bleaching and antiseptics; and polymeric mineral surface active agents such as phosphorylated polymers, in particular polyphosphates that bind to teeth, or metal ions such as stannous, zinc or copper that form insoluble compounds that deposit onto teeth, can be used for erosion protection or sensitivity protection. These actives can be used alone or in combination.

Another example of an additional component includes adhesive components. The present invention may comprise a safe and effective amount of an adhesive component, generally at a level of from about 1% to about 75% by weight of the composition. In other embodiments, the adhesive component is in the range of from about 1%, 5%, 10%, 15%, 20%, 25%, 30%, 35%, 40% to about 10%, 15%, 20%, 50%, 60%, 75%, or any combination thereof. In one particular embodiment, the adhesive component is in an amount from about 10.0% to about 60.0%. In another embodiment, the adhesive component is in an amount from about 1% to about 15%.

In general, adhesive components are hydrophilic particles that become sticky when activated by moisture or are hydrophilic liquids. For those that activate with moisture, moisture can be present, for example, in the oral care composition itself as well as in the oral cavity of the user. In varying embodiments, the adhesive components herein are mucoadhesive, adhesive to the teeth, hydrophilic, water soluble, have the property of swelling upon exposure to moisture, or any combination thereof.

In one embodiment the adhesive component is selected from the group consisting of: glycerin, polyoxamer, sorbitol, polyox, carbomer, polyacrylamides, polypeptides, natural gums; synthetic polymeric gums; AVE/MA; AVE/MA/IB; copolymers of maleic acid or anhydride and ethylene, styrene, and/or isobutylene, polyacrylic acid and/or polyacrylates thereof; polyitaconic acid, mucoadhesive polymers; water-soluble hydrophilic colloids; saccharide; cellulose; cellulosic resin, acrylic resin, their derivatives, and mixtures thereof. Examples of such materials include karaya gum; guar gum; gelatin; algin; sodium alginate; tragacanth; chitosan; acrylamide polymers; carboxypolymethylene; polyvinyl alcohol; polyamines; polyquarternary compounds; polyvinylpyrrolidone or its copolymers; cationic polyacrylamide polymers; salts and mixed salts of AVE/MA; polymeric acids, polymeric salts, and copolymers thereof; polyitaconic acid salts; polyhydroxy compounds; their derivatives; and mixtures thereof.

In another embodiment, the adhesive component is selected from the group consisting of: cellulose, cellulose derivatives (such as methylcellulose, carboxymethylcellulose, hydroxyethylcellulose, hydroxypropylcellulose, hydroxy-propylmethylcellulose, corn starch, and mixtures thereof), starch, starch derivatives, saccharide, saccharide derivatives, polyethylene oxides, polyethylene glycols, polyvinyl alcohols, carrageenan, alginates, karaya gums, xanthan gums, guar gums, gelatins, algins, tragacanth, chitosan, acrylamide polymers, carboxypolymethylenes, polyamines, poly quaternary compounds, polyvinylpyrrolidone, AVE/MA, salts of AVE/MA, mixed salts of AVE/MA, polymeric acids, polymeric salts, polyhydroxy compounds, and mixtures thereof.

Ratios

Furthermore, it has been surprisingly discovered that specific combinations and/or ratios of sweeteners, sensates, and/or flavors, delivered via water-insoluble carriers to the oral cavity provide a high level of consumer recognizable benefits such as fresh feeling, clean feeling, slick teeth, smooth teeth, and fresh breath. In addition, it was also surprisingly discovered that consumer acceptability of a water insoluble carrier based oral care composition was highest when a sweetener is present.

Thus, even though water insoluble carrier systems offer some additional flexibility in formulation from water soluble carrier based systems, there appears to be a particular range of ratios within the system for the sweetener, flavor, and sensate in order to produce a consumer acceptable product. Thus, the compositions of the present invention with the components present in the specific ratios disclosed herein are believed to offer superior flavor benefits to those compositions that do not contain the components disclosed herein or are present in different ratios, and thus, give a more consumer acceptable product. Since consumer acceptance helps drive the use of the product, it is an important feature in the development of a successful product.

The first ratio is the weight of sensate to the weight of flavor ("R1"). This ratio is calculated by dividing the weight percentage of sensate by the weight percentage of flavor. In one embodiment, this ratio is from about 0 to about 4.0. In another embodiment, this ratio is from about 0.25 to about 2.0. In another embodiment, this ratio is about 1.0.

The second ratio is for the weight of flavor to the weight of sweetener in the oral care composition ("R2"). To calculate this ratio, the weight percentage of flavor is divided by the weight percentage of sweetener. In one embodiment, this ratio is from about 0 to about 20. In another embodiment, the ratio is from about 1.0 to about 4.0. In another embodiment, the ratio is from about 1.5 to about 2.5. In a further embodiment, the ratio is about 2.0.

The next ratio is for the weight of sensate to the weight of sweetener ("R3"). This ratio is calculated by dividing the weight percentage of sensate by the weight percentage of sweetener. In one embodiment, this ratio is from about 0 to about 20. In another embodiment, the ratio is from about 1.0 to about 4.0. In another embodiment, the ratio is from about 1.5 to about 2.5. In a further embodiment, the ratio is about 2.0.

The last ratio is the weight of sensates and weight of flavors to the weight of sweetener ("R4"). This ratio is calculated by adding the weight percentage of sensates to the weight percentage of flavors and dividing that total by the weight percentage of sweeteners. In one embodiment, this ratio is from about 0.4 to about 40. In varying embodiments, this ratio is from about 2.0 to about 8.0, from about 3.0 to about 7.0, or from about 3.0 to about 5.0. In an additional embodiment, the ratio is about 4.0.

These ratios can be used to help define a consumer acceptable oral care product for a water insoluble base. For example, in one embodiment, R1 is from about 0.25 to about 4.0, R2 is from about 0.2 to about 20, and R3 is from about 0.2 to about 20. In another embodiment, R1 is from about 0.5 to about 2.0, R2 is from about 1.0 to about 4.0, and R3 is from about 1.0 to about 4.0. In another embodiment, R1 is about 1.0, R2 is about 2.0, and R3 is about 2.0.

Oral Care Compositions

Various combinations of the water insoluble carrier, sweetener, flavor, and/or sensate are possible and are considered within the scope of the invention, a few specific combinations are discussed below.

In one embodiment, an oral care composition comprises a water insoluble carrier, a sweetener, and an additional component selected from a sensate, a flavor, or combination thereof. In another embodiment, an oral care composition consists essentially of a water insoluble carrier, a sweetener, and an additional component selected from a sensate, a flavor, or a combination thereof. Both of these embodiments are configured for application within the oral cavity. In one embodiment, the oral care compositions are configured for application to the teeth.

In a further embodiment, the oral care composition comprises at least 75% by weight of the water insoluble carrier. In another embodiment, the water insoluble carrier is from about 70% to about 99% by weight of the oral care composition. In an additional embodiment, the water insoluble carrier is from about 50% to about 99% by weight of the oral care composition.

In another embodiment, the water insoluble carrier is selected from the group consisting of: rubber, natural wax, synthetic wax, polyvinyl chloride, nylon, fluorocarbon, polyurethane prepolymer, polyethylene, polystyrene, polypropylene, petrolatum, polyvinyl acetate, natural oil, synthetic oil, fats, silicone, hydrocarbons, caprilic/capric triglycerides, oleic acid, stearic acid, and mixtures thereof. In one embodiment, the water insoluble carrier comprises microcrystalline wax, paraffin wax, bees wax, petrolatum, mineral oil, polybutene, silicone, natural oil, synthetic oil, polyethylene, or combinations thereof. In a further embodiment, the water insoluble carrier is selected from the group consisting of polybutene, silicones, petrolatum, and combinations thereof. In another embodiment, the carrier comprises petrolatum. In yet another embodiment, the carrier consists essentially of petrolatum.

In a further embodiment, the oral care composition comprises from about 0.5% to about 10% by weight of a sweetener. In one embodiment, the sweetener is selected from a group consisting of dextrose, fructose, corn syrup, high fructose corn syrup, aspartame, saccharin, sugar alcohols, and mixtures thereof. In a one embodiment, the sweetener is selected from the group consisting of saccharin, sucralose, Rebiana, xylitol, aspartame, Acesulfame K, mono ammoniated glycyrrhizinate, and mixtures thereof. In another embodiment, the sweetener comprises saccharin, sucralose, Rebiana, or a combination thereof.

In another embodiment, the sum of the weight percentages of the sweetener and the additional component is less than about 25%. In another embodiment the sum of the weight percentages of the sweetener and the additional component is less than 25%. In an additional embodiment, the sum of the weight percentages of the sweetener and the additional component is from about 8% to about 15%.

In one embodiment, the additional component comprises a flavor. In a further embodiment, the flavor is selected from the group consisting of: peppermint, spearmint, vanilla, cinnamon, wintergreen, mint, strawberry, grape, apple, and combinations thereof. In a further embodiment, the flavor component comprises mixed mint, peppermint, spearmint, wintergreen, or a combination thereof. In an additional embodiment, the flavor component consists essentially of mint. In one embodiment, the ratio of flavor to sweetener is from about 0.2 to about 20.

In one embodiment, the additional component comprises a sensate. In one embodiment, the sensate comprises a coolant. In another embodiment, the sensate is selected from the group consisting of menthol, menthyl lactate, leaf alcohol, camphor, clove bud oil, eucalyptus oil, anethole, methyl salicylate, eucalyptol, cassia, 1-8 menthyl acetate, eugenol, oxanone, alpha-irisone, propenyl guaethol, thymol, linalool, benzaldehyde, cinnamaldehyde glycerol acetal, and mixtures thereof. In another embodiment, the sensate is selected from the group consisting of menthol; 3-1-menthoxypropane-1,2-diol; methyl lactate; N,2,3-trimethyl-2-isopropylbutanamide; N-ethyl-p-menthan-3-carboxamide; N-(4-cyanomethylphenyl)-p-menthanecarboxamide, and combinations thereof. In a further embodiment, the sensate comprises menthol; N,2,3-trimethyl-2-isopropylbutanamide; N-(4-cyanomethylphenyl)-p-menthanecarboxamide; or a combination thereof. In an additional embodiment, the ratio of sensate to sweetener is from about 0.2 to about 20.

In another embodiment, the additional component comprises a combination of flavor and sensate. In one embodiment, the ratio by weight of flavor plus sensate to sweetener is from about 0.4 to about 40. In another embodiment, the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0. In an additional embodiment, the oral care composition comprises from about 1% to about 10% by weight of flavor and from about 1% to about 10% by weight of sensate.

In one specific embodiment, the oral care composition consists essentially of a water insoluble carrier, a sweetener, and an additional component selected from the group consisting of sensate, flavor, and combinations thereof, wherein the composition is configured for application within the oral cavity. In another specific embodiment, an oral care composition consists essentially of petrolatum, saccharin, mint oil, and menthol and is configured for application to the teeth. In a further embodiment, the ratio by weight of flavor plus sensate to sweetener is from about 0.4 to about 40. In another embodiment, the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0. In another embodiment, the ratio by weight of flavor plus sensate to sweetener is from about 0.4 to about 40. In another embodiment, the ratio by weight of sensate to flavor is about 1.0, the ratio by weight of flavor to sweetener is about 2.0, the ratio by weight of sensate to sweetener is about 2.0, and the ratio by weight of flavor plus sensate to sweetener is about 4.0.

In one embodiment the composition is substantially free of surfactants, abrasives, fluoride sources, therapeutic actives, muco-adhesives, polybutenes, silicones, and/or antimicrobial agents.

In one embodiment, the oral care composition is not a dentifrice. In another embodiment, the oral care composition is not a rinse. In another embodiment, the oral care composition is not a denture adhesive.

In one embodiment, the oral care composition will be in the form of a liquid or gel. The liquid or gel form of the oral care composition may be applied with an applicator. The applicator may be used with any oral care applicator, for example, a swab, brush, foam tipped applicator, etc.

While a few embodiments are discussed above, additional embodiments enabled based on the discussion above, for example specific types of each component, its weight percentages, and ratios, are believed to also be within the scope of the invention.

Methods of Use

The oral care composition as discussed herein may be used to deliver any oral care components compatible with the water insoluble carrier to the oral cavity. For example, an oral care composition may be used as a breath freshener by including a breath freshening agent, like a flavor, in the oral care composition or the composition may be used as an active delivery vehicle by including an active.

Without being limited by theory, it is also believed there will be benefits to a consumer due to the formation of a water insoluble layer on the teeth upon application. Thus, the oral care composition can be used to form a water insoluble barrier on the teeth. Some benefits expected from such a barrier include: reduction in caries, plaque, and calculus due at least in part to the inability of bacteria to stick to the teeth, reduction in sensitivity due at least in part to the blocking of dentin tubules, reduction in erosion and prevention of staining due at least in part to the coating operating as a barrier to erosive agents, and overall improvements in mouth feel impression and/or appearance which can be broadly characterized as aesthetics, such as shine, gloss, luster, smoothness, slickness, and clean mouth feel.

EXAMPLES

Example 1

Various Compositions of the Invention

The following non-limiting examples further illustrate and describe the embodiments of the subject invention wherein both essential and optional ingredients are combined. It is to be understood that the examples are given solely for the purpose of illustration and are not to be construed as limiting the scope of the present invention, as many variations thereof are possible without departing from the spirit and scope of the invention.

|  | A % | B % | C % | D % | E % | F % | G % | H % | I % | J % | K % |
|---|---|---|---|---|---|---|---|---|---|---|---|
| Microcrystalline Wax W835 | 0 | 48 | 0 | 0 | 48 | 0 | 0 | 0 | 10 | 10 | 0 |
| Mineral Oil | 0 | 42 | 0 | 0 | 34 | 0 | 0 | 0 | 0 | 0 | 0 |
| Petrolatum | 90 | 0 | 0 | 82 | 0 | 90 | 89 | 88 | 80 | 79 | 94 |
| Mixed Mint Flavor | 4 | 4 | 4 | 8 | 8 | 8 | 2 | 4 | 4 | 4 | 4 |
| Menthol | 4 | 4 | 4 | 8 | 8 | 1 | 8 | 4 | 4 | 4 | 0 |
| Saccharin (Powder) | 2 | 2 | 2 | 2 | 2 | 1 | 1 | 4 | 2 | 2 | 2 |
| Versagel 750 M (or 1600 M) | 0 | 0 | 90 | 0 | 0 | 0 | 0 | 0 | 0 | 1 | 0 |
|  | 100.0 | 100.0 | 100.0 | 100.0 | 100.0 | 100.0 | 100.0 | 100.0 | 100.0 | 100.0 | 100.0 |
| R1 | 1.00 | 1.00 | 1.00 | 1.00 | 1.00 | 0.13 | 4.00 | 1.00 | 1.00 | 1.00 | 0.00 |
| R2 | 2.00 | 2.00 | 2.00 | 4.00 | 4.00 | 8.00 | 2.00 | 1.00 | 2.00 | 2.00 | 2.00 |
| R3 | 2.00 | 2.00 | 2.00 | 4.00 | 4.00 | 1.00 | 8.00 | 1.00 | 2.00 | 2.00 | 0.00 |
| R4 | 4.00 | 4.00 | 4.00 | 8.00 | 8.00 | 9.00 | 10.00 | 2.00 | 4.00 | 4.00 | 2.00 |

To make the above example compositions B, E, I, and J the wax is melted at 95° C. and the other components are mixed into it at the elevated temperature. To make the above examples A, C, D, F, G, H, and K the petrolatum and/or Versagel is heated to about 70° C. and the other components are mixed in at the elevated temperature. For all examples, the compositions are allowed to come to room temperature prior to use.

Furthermore, each of the above example formulations may also be mixed with each other to provide hybrid-examples.

Example 2

Ratios

|  | A % | B % | c % |
|---|---|---|---|
| Petrolatum | 90 | 92 | 94 |
| Saccharin | 2 | 0 | 2 |

-continued

|  | A % | B % | c % |
|---|---|---|---|
| Mint | 4 | 4 | 0 |
| Menthol | 4 | 4 | 4 |
|  | 100.0 | 100.0 | 100.0 |
| R1 | 1.00 | 1.00 | >100 |
| R2 | 2.00 | >100 | 0.00 |
| R3 | 2.00 | >100 | 2.00 |
| R4 | 4.00 | >100 | 2.00 |

To make the above examples A, B, and C, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). Each of Samples B and C are directly compared with Sample A, so each consumer tests Sample A versus Sample B, then Sample A versus Sample C. The preferences and ratings for these comparisons are below.

|  | Sample A vs. Sample B | Sample A vs. Sample C |
|---|---|---|
| Rating | Sample A is preferred over Sample B by 100% of the Panelists | Sample A is preferred over Sample C by 67% of the Panelists |
|  | Sample A is rated: 2.4 | Sample A is rated: 2.11 |
|  | Sample B is rated: −1.8 | Sample C is rated: 0.67 |

The above results indicate Sample A is strongly preferred over and rated much higher than Sample B. Specifically, Sample A, with R1/R2/R3/R4 ratios of 1/2/2/4, is strongly preferred over and rated much higher than Sample B with R1/R2/R3/R4 ratios of 1/>100/>100/>100.

The above results also indicate that Sample A is preferred over and rated higher than Sample C. Specifically, Sample A, with R1/R2/R3/R4 ratios of 1/2/2/4, is preferred over and rated higher than Sample B with R1/R2/R3/R4 ratios of >100/0/2/2.

Example 3

Ratios

|  | A % | B % | C % | D % |
|---|---|---|---|---|
| Petrolatum | 91.8 | 98.5 | 91.8 | 90 |
| Saccharin | 0.16 | 0.3 | 0.16 | 2 |
| Mint | 4 | 0.6 | 4 | 4 |
| Menthol | 4 | 0.6 | 4 | 4 |
|  | 100.0 | 100.0 | 100.0 | 100.0 |
| R1 | 1.00 | 1.00 | 1.00 | 1.00 |
| R2 | 25.00 | 2.00 | 25.00 | 2.00 |
| R3 | 25.00 | 2.00 | 25.00 | 2.00 |
| R4 | 50.00 | 4.00 | 50.00 | 4.00 |

To make the above examples A, B, C, and D, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). The preferences and ratings for these comparisons are below.

|  | Sample A vs. Sample B | Sample C vs. Sample D |
|---|---|---|
| Rating | Sample B is preferred over Sample A by 75% of the Panelists<br>Sample A is rated: 0.63<br>Sample B is rated: 1.75 | Sample D is preferred over Sample C by 90% of the Panelists<br>Sample C is rated: 0.9<br>Sample D is rated: 2.3 |

The above results indicate Sample B is preferred over and rated higher than Sample A. Specifically, Sample B, with R1/R2/R3/R4 ratios of 1/2/2/4, is preferred over and rated higher than Sample A with R1/R2/R3/R4 ratios of 1/25/25/50.

The above results also indicate that Sample D is strongly preferred over and rated much higher than Sample C. Specifically, Sample D, with R1/R2/R3/R4 ratios of 1/2/2/4, is strongly preferred over and rated much higher than Sample C with R1/R2/R3/R4 ratios of 1/25/25/50.

Example 4

Level

|  | A % | B % |
|---|---|---|
| Petrolatum | 98.5 | 90.0 |
| Saccharin | 0.3 | 2 |
| Mint | 0.6 | 4 |
| Menthol | 0.6 | 4 |
|  | 100.0 | 100.0 |
| R1 | 1.00 | 1.00 |
| R2 | 2.00 | 2.00 |
| R3 | 2.00 | 2.00 |
| R4 | 4.00 | 4.00 |

To make the above examples A and B, the petrolatum is heated to about 70° C. and the other components are mixed in at the elevated temperature. For all examples, the compositions are allowed to come to room temperature prior to use. After the samples are made, they are placed into a container. The consumer preference for taste is tested by allowing a consumer to dip a disposable lip gloss applicator into the container and tasting the sample. The consumer then picks the sample they prefer. The consumer also rates each sample on a scale of −4 to +4 (with −4 being "Dislike Extremely" and +4 being "Like Extremely"). The preferences and ratings for these comparisons are below.

|  | Sample A vs. Sample B |
|---|---|
| Rating | Sample B is preferred over Sample A by 80% of the Panelists<br>Sample A is rated: 0.5<br>Sample B is rated: 1.8 |

The above results indicate Sample B is preferred over and rated higher than Sample A. Specifically, Sample B, with a total Saccharin+Mint+Menthol level of 10% [and R1/R2/R3/R4 ratios of 1/2/2/4], is preferred over and rated higher than Sample A with total Saccharin+Mint+Menthol level of 1.5% [and the same R1/R2/R3/R4 ratios of 1/2/2/4].

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition, comprising:
   a) at least about 75% by weight of the oral care composition of a water insoluble carrier selected from the group consisting of natural oils, synthetic oils, petrolatum, and combinations thereof,
   b) a sweetener;
   c) a flavor; and
   d) a sensate, wherein the sensate imparts a warming sensation, a cooling sensation, and/or a tingling sensation to the oral cavity;
   wherein the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0; and
   wherein the oral care composition is configured for application within the oral cavity, is in the form of a liquid or gel and is substantially free of surfactants, abrasives, fluoride sources, therapeutic actives, muco-adhesives, polybutenes, silicones, and antimicrobial agents 2. The oral care composition of claim 1, wherein the oral care composition is configured for application to the teeth.

3. The oral care composition of claim 2, further comprising a monoalkyl phosphate.

4. The composition of claim 1, wherein the sum of the weight percentage of components (b) and (c) is less than 25%.

5. The composition of claim 1, wherein the sum of the weight percentage of components (b) and (c) is from about 8% to about 15%.

6. The composition of claim 1, wherein the water insoluble carrier is petrolatum.

7. An oral care composition, consisting essentially of:
   a) at least about 75% by weight of the oral care composition of petrolatum;
   b) saccharin;
   c) mint oil; and
   d) menthol;
   wherein the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0; and
   wherein the composition is configured for application to the teeth, is in the form of a liquid or gel and is substantially free of surfactants, abrasives, fluoride sources, therapeutic actives, muco-adhesives, polybutenes, and silicones.

8. An oral care composition, comprising:
   a) from about 80% to about 99% by weight of petrolatum,
   b) from about 0.5% to about 10% by weight of a sweetener,
   c) from about 1% to about 10% by weight of the oral care composition of flavor, and
   d) from about 1% to about 10% by weight of the oral care composition of sensate, wherein the sensate imparts a warming sensation, a cooling sensation, and/or a tingling sensation to the oral cavity,
   wherein the ratio by weight of sensate to flavor is from about 0.5 to about 2.0, the ratio by weight of flavor to sweetener is from about 1.0 to about 4.0, the ratio by weight of sensate to sweetener is from about 1.0 to about 4.0, and the ratio by weight of flavor plus sensate to sweetener is from about 2.0 to about 8.0;
   wherein the oral care composition is configured for application within the oral cavity, is in the form of a liquid or gel and is substantially free of surfactants, abrasives, fluoride sources, therapeutic actives, muco-adhesives, polybutenes, silicones, and antimicrobial agents.

9. The oral care composition of claim 8 wherein the sweetener is selected from the group consisting of saccharin, sucralose, Rebiana, xylitol, aspartame, Acesulfame K, mono ammoniated glycyrrhizinate, and mixtures thereof.

10. The oral care composition of claim 9, wherein the sensate is selected from the group consisting of menthol; 3-1-menthoxypropane-1,2-diol, menthyl lactate; N,2,3-trimethyl-2-isopropylbutanamide; N-ethyl-p-menthan-3-carboxamide; N-(4-cyanomethylphenyl)-p-menthanecarboxamide, and combinations thereof.

11. The oral care composition of claim 7, wherein the total saccharin+mint+menthol level is 10% and the wherein the ratio by weight of sensate to flavor is 1, the ratio by weight of flavor to sweetener is 2, the ratio by weight of sensate to sweetener is 2, and the ratio by weight of flavor plus sensate to sweetener is 4.

12. The oral care composition of claim 7, wherein the weight percentage of the sum of components (b), (c), and (d) is from about 8% to about 15%.

* * * * *